United States Patent
Corcos et al.

(10) Patent No.: US 9,217,673 B2
(45) Date of Patent: Dec. 22, 2015

(54) HIGH RESPONSIVITY DEVICE FOR THERMAL SENSING IN A TERAHERTZ RADIATION DETECTOR

(71) Applicant: International Business Machines Corporation, Armonk, NY (US)

(72) Inventors: Dan Corcos, Nesher (IL); Danny Elad, Moshav Liman (IL); Noam Kaminski, kiryat tivon (IL); Bernhard Klein, Zürich (SZ); Lukas Kull, Zurich (SZ); Thomas Morf, Gross (SZ)

(73) Assignee: GLOBALFOUNDRIES INC., Grand Cayman (KY)

( * ) Notice: Subject to any disclaimer, the term of this patent is extended or adjusted under 35 U.S.C. 154(b) by 0 days.

(21) Appl. No.: 14/287,872

(22) Filed: May 27, 2014

(65) Prior Publication Data

US 2014/0284483 A1    Sep. 25, 2014

Related U.S. Application Data (62) Division of application No. 13/663,511, filed on Oct. 30, 2012.

(51) Int. Cl.
*G01J 5/00* (2006.01)
*G01J 5/20* (2006.01)
(Continued)

(52) U.S. Cl.
CPC ......... *G01J 5/20* (2013.01); *G01J 5/0837* (2013.01); *G01N 21/3581* (2013.01); *H01Q 21/26* (2013.01)

(58) Field of Classification Search
CPC .................................................. G01N 21/3581
USPC ....................................................... 250/338.1
See application file for complete search history.

(56) References Cited

U.S. PATENT DOCUMENTS

2002/0006154 A1*  1/2002  Nada ............................. 374/169
2006/0231761 A1   10/2006  Peytavit et al.
(Continued)

FOREIGN PATENT DOCUMENTS

WO   2011151756   12/2011

OTHER PUBLICATIONS

Vitiello, M.S. et al., "Room Temperature Terahertz Detectors based on Semiconductor Nanowire Field Effect Transistors", Proc. SPIE 8268, Quantum Sensing and Nanophotonic Devices IX, 826829, Jan. 20, 2012.

(Continued)

*Primary Examiner* — David Porta
*Assistant Examiner* — Abra Fein
(74) *Attorney, Agent, or Firm* — DeLio, Peterson & Curcio, LLC; Peter W. Peterson (57) ABSTRACT

There is provided a high responsivity device for thermal sensing in a Terahertz (THz) radiation detector. A load impedance connected to an antenna heats up due to the incident THz radiation received by the antenna. The heat generated by the load impedance is sensed by a thermal sensor such as a transistor. To increase the responsivity of the sense device without increasing the thermal mass, the device is located underneath a straight portion of an antenna arm. The transistor runs substantially the entire length of the antenna arm alleviating the problem caused by placing large devices on the side of the antenna and the resulting large additional thermal mass that must be heated. This boosts the responsivity of the pixel while retaining an acceptable level of noise and demanding a dramatically smaller increase in the thermal time constant.

12 Claims, 6 Drawing Sheets

(51) Int. Cl.
  *G01N 21/3581* (2014.01)
  *G01J 5/08* (2006.01)
  *H01Q 21/26* (2006.01)

(56) References Cited

U.S. PATENT DOCUMENTS

2007/0278407 A1   12/2007   Wood et al.
2008/0149811 A1*  6/2008   Kim .............................. 250/205
2008/0251870 A1   10/2008   Morf et al.
2009/0009154 A1*  1/2009   Morf et al. ................. 324/76.19
2011/0062329 A1*  3/2011   Ben-Bassat ................... 250/330
2011/0315880 A1   12/2011   Nemirovsky
2012/0091342 A1   4/2012   Berger et al.

OTHER PUBLICATIONS

Ouyang, Zhengbiao et al., "A Combined Cavity for High Sensitivity THz Signal Detection", Proceedings of SPIE—The International Society for Optical Engineering, vol. 6840, Nov. 12-14, 2007.

* cited by examiner

HIGH RESPONSIVITY DEVICE FOR THERMAL SENSING IN A TERAHERTZ RADIATION DETECTOR

CROSS-REFERENCE TO RELATED APPLICATIONS

This application is a divisional of U.S. patent application Ser. No. 13/663,511, filed Oct. 30, 2012 and entitled "High Responsivity Device for Thermal Sensing in a Terahertz Radiation Detector".

FIELD OF THE INVENTION

The present invention relates to the field of semiconductor imaging devices, and more particularly relates to a high responsivity device for thermal sensing in a Terahertz (THz) radiation detector.

BACKGROUND OF THE INVENTION

THz radiation imaging is currently an exponentially developing research area with inherent applications such as THz security imaging which can reveal weapons hidden behind clothing from distances of ten meters or more; or medical THz imaging which can reveal, for example, skin cancer tumors hidden behind the skin and perform fully safe dental imaging. Constructing prior art THz detectors is typically a challenging endeavor since both radiation sources and radiation detectors are complex, difficult and expensive to make.

THz radiation is non-ionizing and is therefore fully safe to humans unlike X-ray radiation. THz imaging for security applications, for example, uses passive imaging technology, namely the capabilities of remote THz imaging without using any THz radiation source thus relying solely on the very low power natural THz radiation which is normally emitted from any room temperature body according to well-known black body radiation physics. Passive THz imaging requires extremely sensitive sensors for remote imaging of this very low power radiation. Prior art passive THz imaging utilizes a hybrid technology of superconductor single detectors cooled to a temperature of about 4 degrees Kelvin which leads to extremely complex (e.g., only the tuning of the temperature takes more than 12 hours before any imaging can take place) and expensive (e.g., $100,000 or more) systems. A detector is desirable that can be used to detect THz radiation and that has much lower potential cost compared with existing superconducting solutions. Passive THz imaging, however, requires three orders of magnitude higher sensitivity compared with passive infrared (IR) imaging, which is a challenging gap.

SUMMARY OF THE INVENTION

There is provided a high responsivity device for thermal sensing in a Terahertz (THz) radiation detector. A load impedance connected to an antenna heats up due to the incident THz radiation received by the antenna. The heat generated by the load impedance is sensed by a thermal sensor such as a transistor. To increase the responsivity of the sense device without increasing the thermal mass, the device is located underneath a straight portion of an antenna arm.

The transistor thus runs substantially the entire length of the antenna arm. This alleviates the problem caused by placing large devices on the side of the antenna in that the additional area taken up by the sensor transistor translates to a large additional thermal mass that must be heated by the radiation signal. By placing the sensor below the antenna, a considerably smaller "area penalty" is paid. Such a solution allows boosting the responsivity of the pixel while still retaining an acceptable level of noise and demanding a dramatically smaller increase in the thermal time constant.

BRIEF DESCRIPTION OF THE DRAWINGS

The invention is herein described, by way of example only, with reference to the accompanying drawings, wherein.

DETAILED DESCRIPTION OF THE INVENTION

The invention provides a high responsivity device for thermal sensing in an apparatus for detection of Terahertz (THz) radiation. The high responsivity device pertains to the field of Terahertz (THz) wave imaging which is the visualization by detection of THz radiation being irradiated or reflected from objects in the imager's field of view. Apart from being a non-ionizing radiation, the wavelengths of the THz portion of the electromagnetic (EM) spectrum are able to penetrate through numerous things such as fog, clothing, packages, etc., enabling imaging with high resolution even by means of relatively small radiating aperture which is crucial in space constrained environments. These qualities make imaging in this part of the electromagnetic spectrum a prime candidate for use in security, surveillance, navigation, etc. systems.

Figure 1:
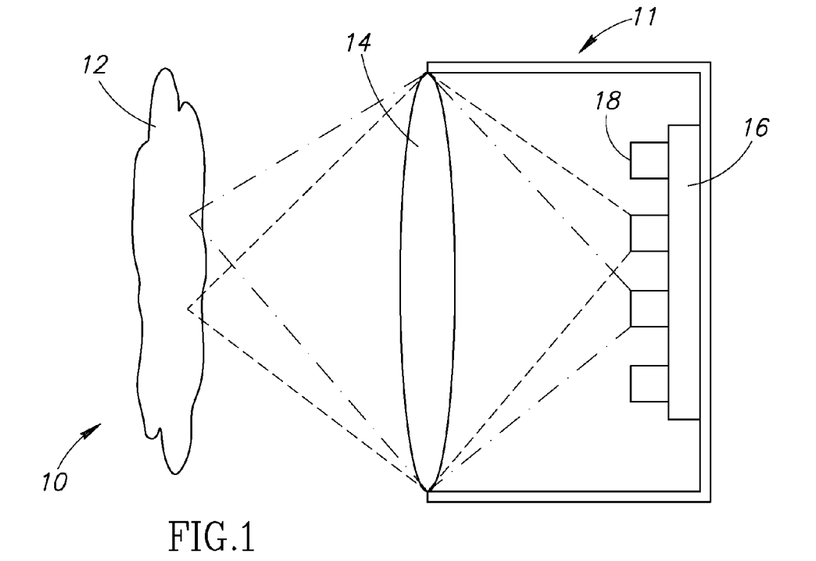
FIG. 1 is a diagram illustrating the structure of an example bolometer for detecting THz radiation.

A diagram illustrating the structure of an example bolometer for detecting THz radiation is shown in FIG. 1. The bolometer, generally referenced 10, comprises the body under test (BUT) 12, lens 14, housing 11, pixel array 18 and read out circuitry 16.

The detection of the THz radiation is performed by an antenna with a resistive load, directed at a specific pixel on the body under test (BUT). The antenna converts the THz electromagnetic energy into electrical current that heats the resistive load. The temperature change of this resistor is then measured as an indication of the temperature of the body under test (BUT).

Sensors at THz frequencies are typically Bolometers, since electronics cannot reach these frequencies. Bolometers can be implemented using slightly modified CMOS techniques or using a CMOS SOI process with MEMS post processing. A THz sensor can be directly integrated with readout circuitry in a CMOS-SOI process. One sensor that can be used is an antenna coupled bolometer. The THz sensor is realized with a temperature dependent resistor or with a FET where its strongly temperature dependent subthreshold current is used as a sensor.

A bolometer based detector may be coupled with a lens on the top of the structure to collect the incident electromagnetic energy of individual pixels. Each pixel is adapted to be thermally isolated from other pixels and from the entire structure. This is achieved by creating a vacuum around the bolometers. In order to increase the sensitivity of the bolometer, the noise is often reduced by cooling the entire structure and the antenna down to cryogenic temperatures.

An imaging device (i.e. an imager or detector) may comprise a 2D array of elements (i.e. pixels), situated as linear arrays or even by single elements that are optically or mechanically scanned. Imaging systems can be either passive (only receiving) or active (illuminating the target) and usually include suitable optical components. An uncooled passive THz system is particularly attractive due to the potentially low manufacturing (and operating) cost and because it does not involve health-related risks.

In general terms, the detection process can be decomposed to following three steps: (1) reception of the incoming radiation impinging the pixel; (2) conditioning of the electromagnetic signal (e.g., filtering, amplification, transduction, etc.); and (3) read out by an electronic circuit.

The present invention deals with the challenges presented by the detection of signals having long wavelengths (sub-millimeter waves) using antenna coupled thermal sensing devices. In particular, the invention relates to the second step, namely the efficient transduction of the electromagnetic signal (THz signal) into a measurable electrical quantity when using a thermal sensor.

Uncooled THz imagers such as resistive self-mixing sensors and bolometric sensors (based on resistive bolometers) do not provide a low enough Noise Equivalent Temperature Difference (NETD) for enabling passive THz imaging systems. Imagers based on coherent heterodyne detectors, which are theoretically limited only by quantum noise, are capable of uncooled passive imaging.

Sensors based on the resistive self-mixing approach are limited to an NEP of approximately 66 $pW/Hz^{1/2}$ which is too large for passive imaging.

The bolometric type of sensors can be further classified into capacitively coupled and directly coupled sensors. In the first kind of detector an antenna is used for receiving the THz power, which is conveyed to a termination resistor. This resistor is physically separated from the antenna by a vacuum gap, which also forms two capacitors (one on each edge of the resistor). The power that is dissipated on the resistor heats up the thermally isolated structure in which the resistor is located and the consequent temperature shift is detected by with a sensing device. The absence of a physical contact between the antenna and the load is necessary for separating their thermal response.

In the case of sub-millimeter waves, the size of the antenna causes its thermal mass to be quite large and thus the heat up time of a pixel lacking capacitive coupling is excessively slow. Thermal time constants longer than ~100 msec degrade the imager's performance when the sensors are used for real time imaging and the read-out time is multiplexed (which is a very attractive configuration for a sensor array). While the capacitive coupling solution allows, in theory, better antenna performance (i.e. big area corresponds to large gain) and good thermal performance, its implementation with a batch micromachining (MEMS) process is rather complex. Tolerances in the pixel geometry due to residual mechanical stress cause a large uncertainty on the final position of the elements, including the capacitor plates. As a consequence, realistically achievable values of the capacitance provide a bottleneck for the coupling efficiency and hence for the sensor's sensitivity. Relatively good performance can still be achieved with this solution provided that sophisticated technical solutions are adopted resulting in higher fabrication complexity.

Directly coupled sensors address the same problem with the opposite approach. This method requires using tiny antennas with a small thermal mass that are turned by micromachining into suspended and thermally isolated structures. Their implementation is feasible for CMOS compatible bulk micromachining, which is a relatively low cost batch fabrication process. The electromagnetic performance of the antennas is, however, poorer than their larger mass counterparts. Here, the need to limit the thermal mass of the entire pixel (i.e. the antenna and the sensing resistor/transistor/diode) forces the use of smaller sensing devices, which are prone to higher electrical noise.

Figure 2:
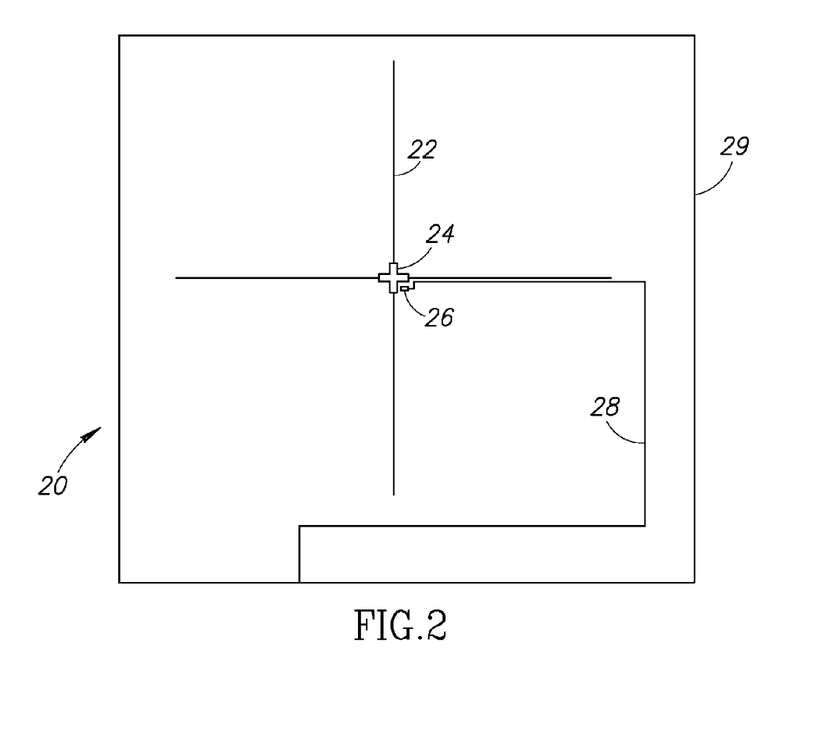
FIG. 2 is a diagram illustrating a first example embodiment cross dipole antenna incorporating a thermal sensor.

A diagram illustrating a first example embodiment cross dipole antenna incorporating a thermal sensor is shown in FIG. 2. The detector, generally referenced 20, comprises a cross dipole antenna element 22, load impedance 24, thermal sensor 26 placed on the side of the antenna and holding arm 28 connected to the substrate 29. The inset of the sensor comprises an NMOS transistor with W/L=3.6 μm/0.36 μm directly connected to the holding arm.

As opposed to an implementation of a directly coupled sensor, where a small temperature sensing device (e.g., transistor) 26 is placed on the side of the antenna 24, a detector is provided incorporating a device located underneath any straight segment of the antenna. In one embodiment, the size of the device (e.g., the transistor's width) is the longest that fits beneath the antenna. In another embodiment, multiple devices, placed under different segments, are connected in parallel (or series) thereby increasing the effective device size.

Figure 3:
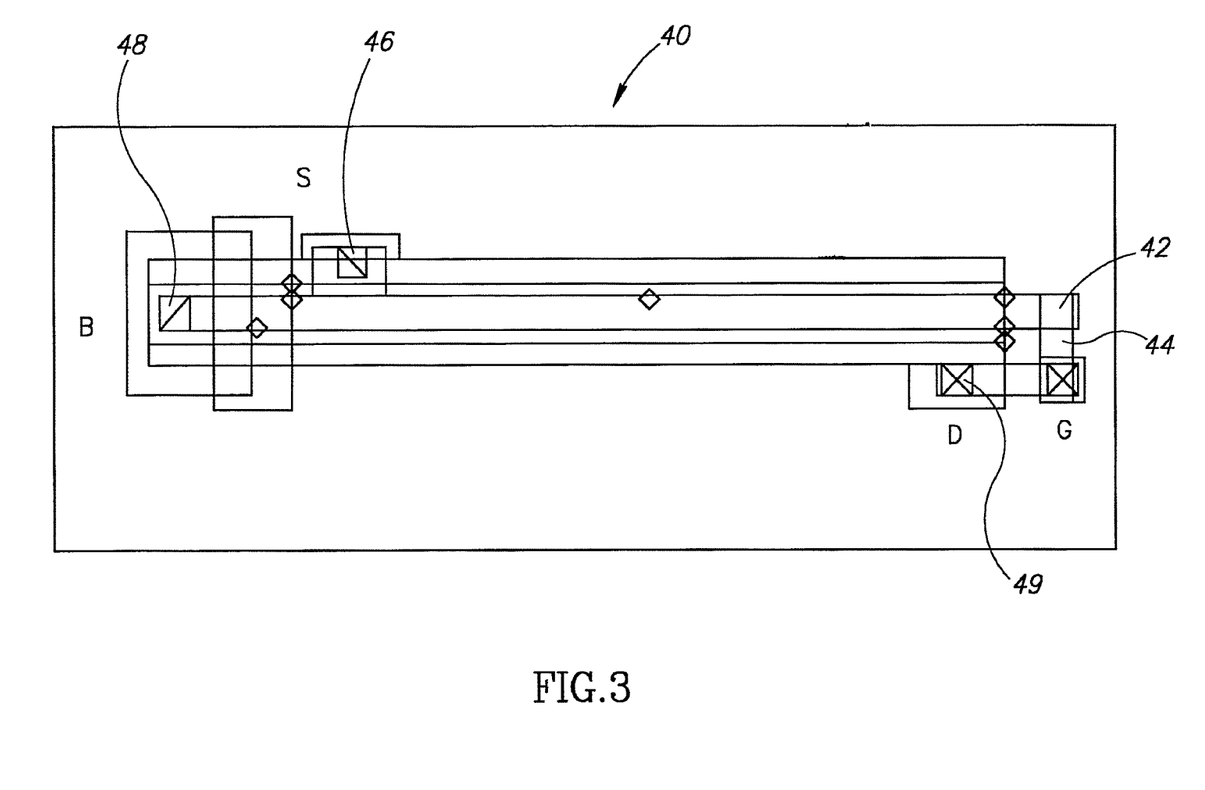
FIG. 3 is a diagram illustrating an example layout of an NMOS transistor where the arm of a dipole antenna overlaps the gate of the transistor over its entire length.

A diagram illustrating an example layout of an NMOS transistor where the arm of a dipole antenna overlaps the gate of the transistor over its entire length is shown in FIG. 3. The layout, generally referenced 40, comprises a metal antenna arm 42 that lies over a long transistor. The transistor comprises a gate 44 that lies under the metal arm, drain connection 49, source connection 46 and body (bulk) connection 48. The transistor thus runs substantially the entire length of the antenna arm. This alleviates the problem caused by placing large devices on the side of the antenna in that the additional area taken up by the sensor transistor translates to a large additional thermal mass that must be heated by the radiation signal. By placing the sensor below the antenna, a considerably smaller "area penalty" is paid. Such a solution allows boosting the responsivity of the pixel while still retaining an acceptable level of noise and demanding a dramatically smaller increase in the thermal time constant.

Figure 4:
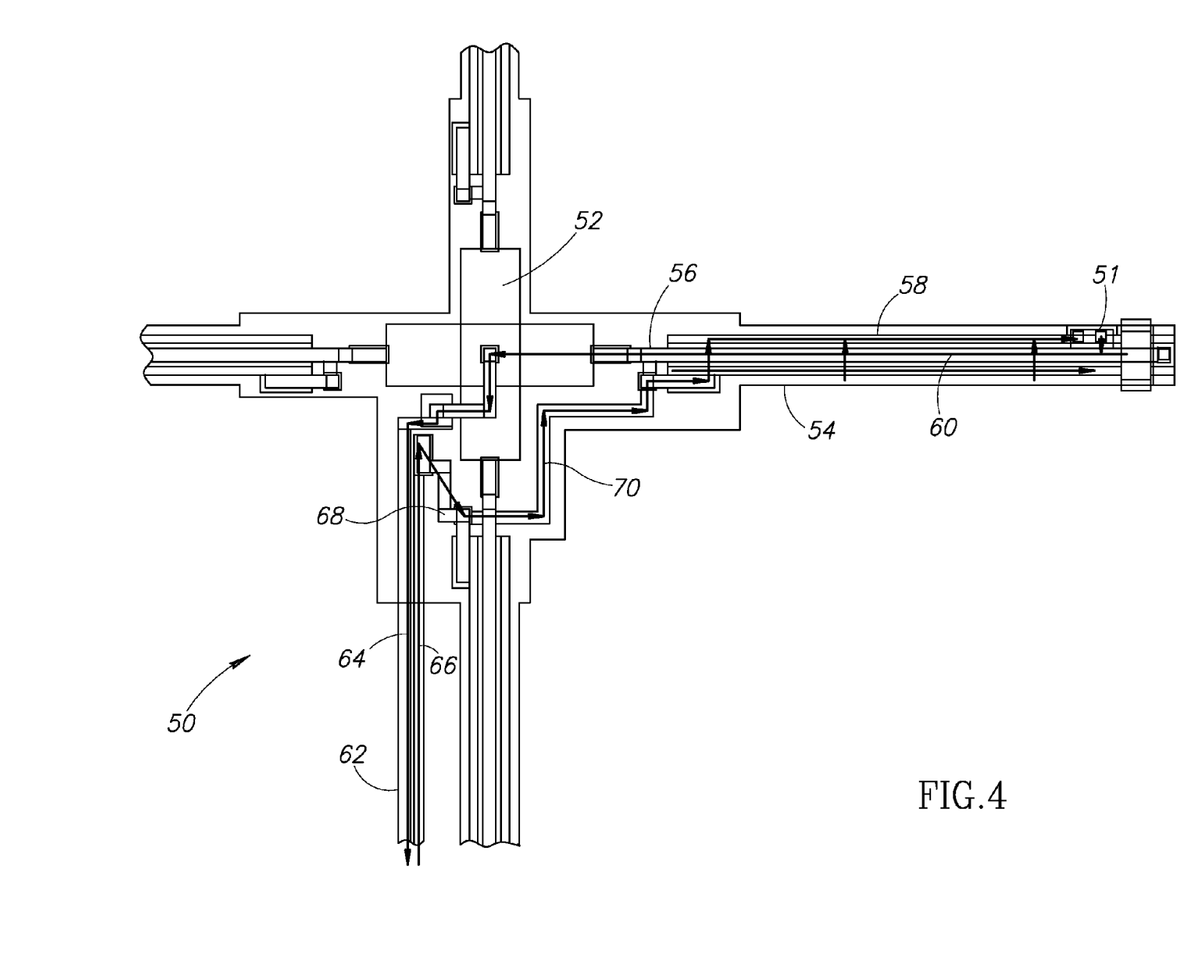
FIG. 4 is a diagram illustrating a second example embodiment cross dipole antenna incorporating a thermal sensor located underneath a dipole arm.

A diagram illustrating a second example embodiment cross dipole antenna incorporating a thermal sensor located underneath a dipole arm is shown in FIG. 4. The detector, generally referenced 50, comprises an antenna arm 54, load impedances 52 and holding arm 62. The antenna arm comprises a metal wire dipole antenna 56 and thermal sense transistor including source and drain 58 and gate 60. The holding arm comprises conductors 64 and 66 for carrying the readout signal to external circuitry. The thermal sensor transistor for detecting the change in heat of the load impedance is located directly beneath the antenna arm. A pair of NMOS transistors with W/L=98 μm/0.2 μm are connected through the antenna arms and load.

The thermal sensor that is used for detecting temperature variations in directly coupled pixels may comprise any electrical device whose I-V characteristic is temperature dependent. For example, the thermal sensor may comprise one or more transistors, diodes and resistors. A transistor is considered to be a good choice since it provides high temperature responsivity (up to 8%/° C.), which translates to large current or voltage responsivity, even when it is biased with low static power.

Note that the bias current applied to the sensor transistor should be sufficiently large to yield large responsivity. The bias voltage is applied through the wires 64, 66 in the holding arm 62. This can be achieved by increasing the bias voltage and/or by increasing the size of the device. The latter option is preferable since a larger device size exhibits reduced noise power spectral density (PSD), whereas a higher gate voltage would raise the noise level for any given device size. Note also that in other implementations the size of the sensing transistor is severely constrained by the pixel's response time requirements (i.e. the thermal time constant). It is thus preferable to have a large transistor whose area approximately overlaps the antenna's area, thus not requiring a large amount of additional area.

The performance of the detector implementation of FIG. 2 and that of FIG. 4 is presented in Table 1 below.

TABLE 1

Comparison of the detector of FIG. 2 (thermal sensor on the side of the antenna) and FIG. 4 (thermal sensor underneath the antenna arm).

| | Transistor size W/L | Time constant T | Noise current PSD at $I_{DS} = 1$ μA |
|---|---|---|---|
| FIG. 2 (small transistor) | 3.6 μm/0.36 μm | 160 msec | 93 pA/Hz$^{1/2}$ |
| FIG. 4 (large transistor) | 2 × 98 μm/0.2 μm | 276 msec | 17 pA/Hz$^{1/2}$ |

The data in Table 1 shows that locating the transistor under the antenna arm provides a huge increase in transistor area (~times 30) while only causing a modest increase in the time constant (~1.7).

The thermal capacitance, as well the thermal time constant, are directly proportional to the volume of the "platform" (namely the antenna and the sensor) as shown by the following expressions.

$$C_{th,obj} = C_{p,obj} \rho_{obj} V_{obj} \quad (1)$$

$$\tau \approx R_{arm}(C_{arm} + C_{ant} + C_{sens}) \quad (2)$$

where $C_{th}$ is the specific heat capacitance per unit mass, $\rho$ the density, V the volume, $R_{arm}$ the heat resistance of the holding arm. Furthermore, the noise PSD for an equal current, while operating in the proximity of or below the threshold voltage, scales down linearly with power. The noise current is often described by the empirical expression given by $$S_I \approx \frac{KF(V_{GS}) \cdot I_{DS}^\alpha}{(C_{ox}\|C_s) \cdot L_{eff}^\beta \cdot W_{eff}^{\alpha-1}} \frac{1}{f} \quad (3)$$

where KF is the technological flicker noise parameter, $I_{DS}$ the transistor's current, $C_{ox}$ and $C_s$ the oxide and surface capacitance respectively, $W_{eff}$ and $L_{eff}$ the effective width and length of the gate, f the frequency. In the case presented in Table 1 supra we assume that $\alpha=2$, $\beta=1$, $C_{ox}\|C_s \approx C_{ox}$. In order to reduce noise, either W or L may be increased at the lower bias, while large L is more effective at high bias.

Note that care should be devoted to the electrical connections of the antenna and the thermal sensor. For example, in the case of a dipole antenna, if the DC carrying wires were to be placed on the side of the device, the required area would grow considerably. Hence, the sensor wiring preferably takes advantage of and blends with the electrical connections of the antenna without impacting its electromagnetic performance. This is achieved by using the antenna "arm" under which the sensor lies as a conductor for the DC bias. Since from the point of view of the RF signal, the middle point of the load resistor is fixed in potential. Thus, a DC source can be connected at that point without changing the impedance seen by the antenna and without degrading its RF performance. Consequently, the circuit can be closed on one side (i.e. on the dipole's furthest edge) by the connection to the source pin 51 of the transistor, and on the other side by the voltage supplied to the middle of the load resistance 52. Furthermore, the parasitic resistance across the holding arm provides RF choking towards the read out circuit, isolating the RF from the DC signal. The voltage drop on this portion of the resistor is a parasitic effect. This, however, is typically negligible since the termination resistors are typically much smaller than 1 kΩ and the bias currents are on the order of microamperes. The arrows in FIG. 4 highlight the DC bias current path through the holding arm wires, paths 68, 70, one antenna arm 54 and load impedance 52. Note that this approach is significantly different from implementations of directly coupled pixels were the antenna and the thermal sensor are coupled thermally but not electrically.

Figure 5A:
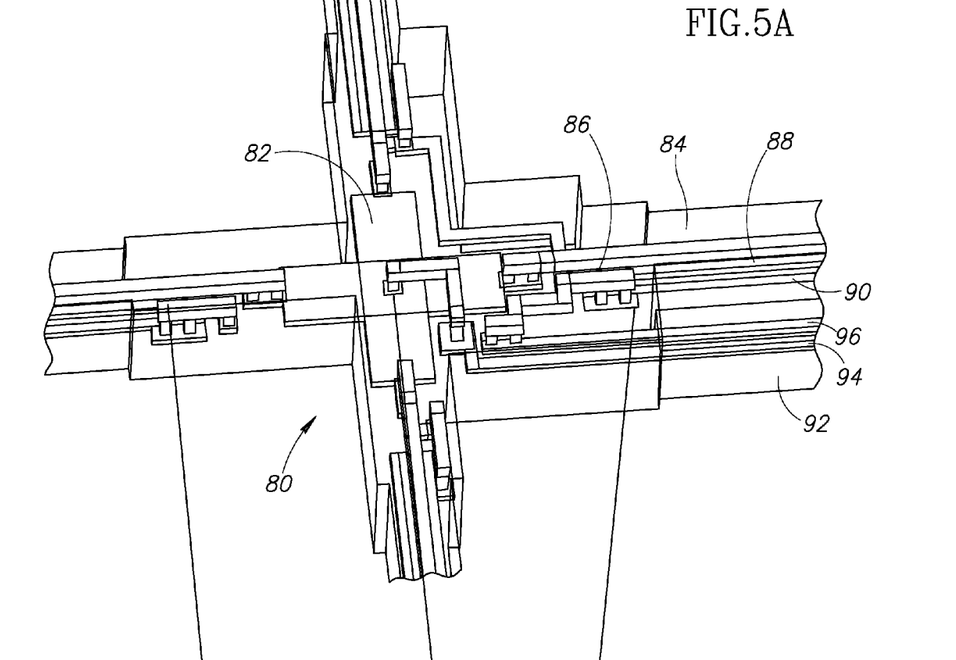
FIG. 5A is a perspective view of a portion of the detector of FIG. 4.

A perspective view of a portion of the detector of FIG. 4 is shown in FIG. 5A. The detector, generally referenced 80, comprises antenna arm 84 (partially shown) connected to load impedance 82, and holding arm 92. The holding arm comprises readout and bias wires 94, 96. Antenna arm comprises dipole wire 86 and transistor 90 that lies thereunder, including gate 88.

Figure 5B:
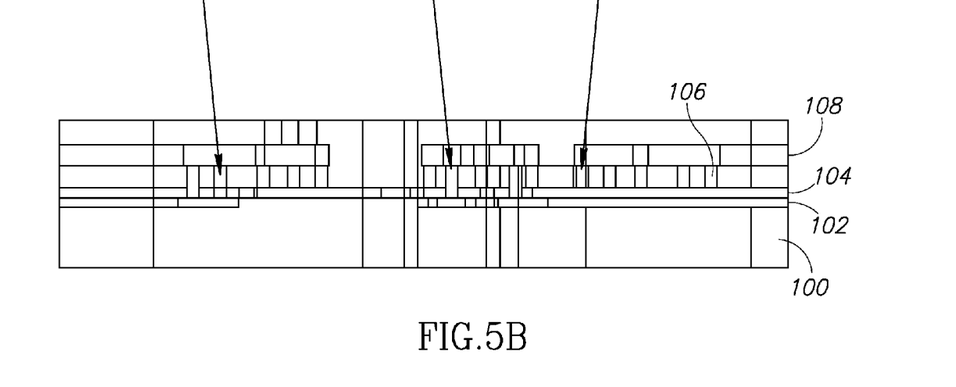
FIG. 5B is a side view of a portion of the detector of FIG. 4.

A side view of a portion of the detector of FIG. 4 is shown in FIG. 5B. The various layers shown include silicon oxide 100, active silicon 102, polysilicon 104, tungsten vias 106 and copper metal layer 108. The polysilicon gate layer 104 of the sense transistor runs underneath along the length of the metal antenna arm 108.

Figure 6A:
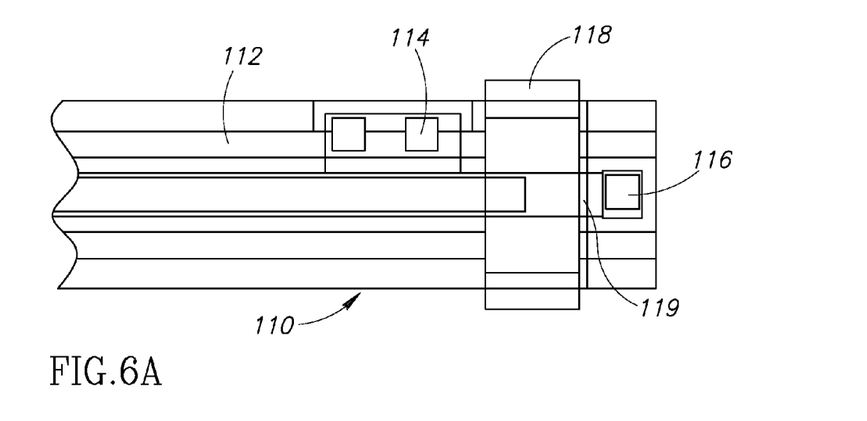
FIG. 6A is a diagram illustrating the end portion of a dipole arm located over the thermal sensor transistor.

A diagram illustrating the end portion of a dipole arm located over the thermal sensor transistor is shown in FIG. 6A. The portion of the antenna arm shown, generally referenced 110, comprises a transistor 112, including drain and source sides, source contact 114, polysilicon gate 118, body contact 116 and metal dipole arm 119. The gate of the sensor transistor runs underneath the metal dipole arm.

Figure 6B:
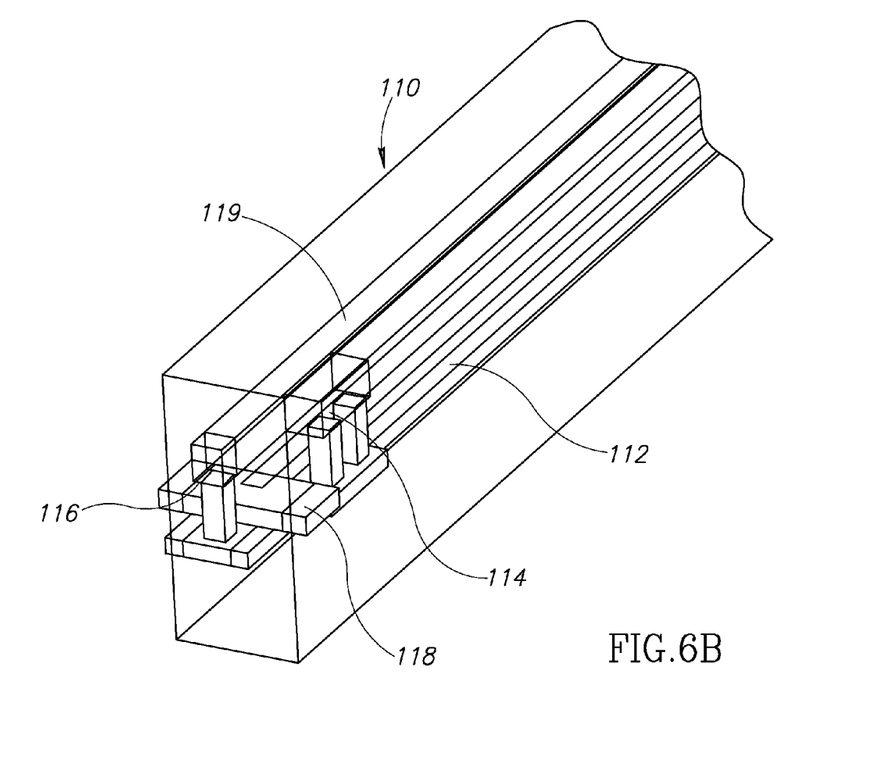
FIG. 6B is a perspective view of the end portion of a dipole arm located over the thermal sensor transistor.

A perspective view of the end portion of a dipole arm located over the thermal sensor transistor is shown in FIG. 6B. Shown in perspective view of the arm, generally referenced 110, are the source and drain 112 of the sensor transistor source contact 114, polysilicon gate 118, body contact 116 and metal dipole arm 119.

Figure 7A:
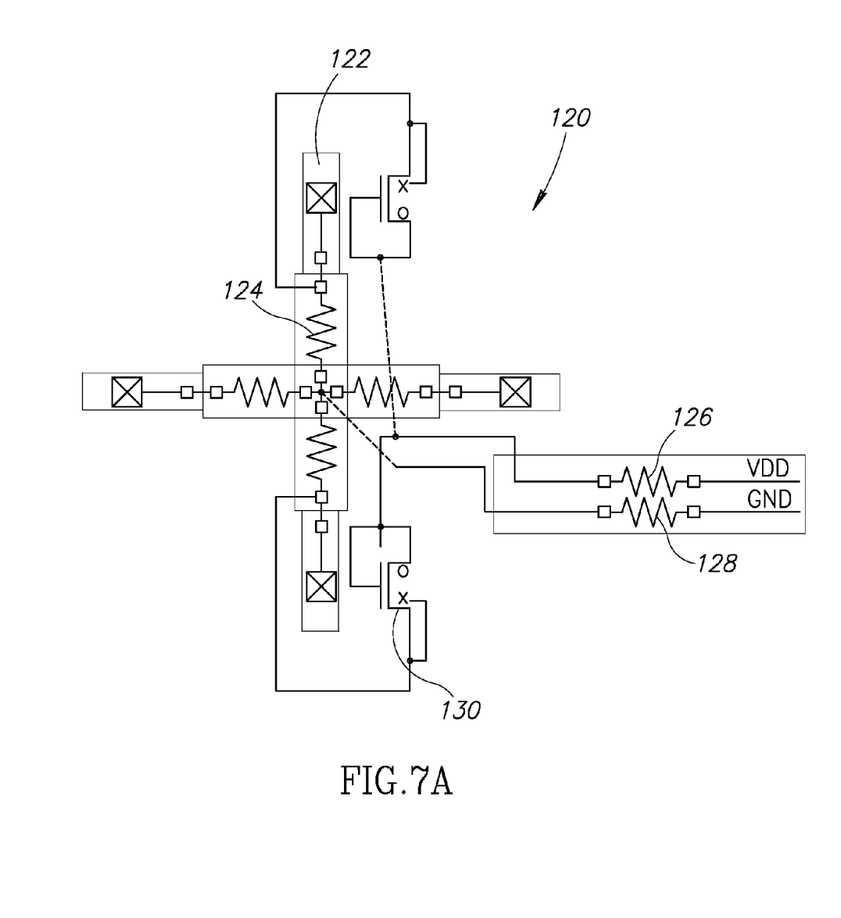
FIG. 7A is a diagram illustrating the electrical model of the detector of FIG. 4.

A diagram illustrating the electrical model of the detector of FIG. 4 is shown in FIG. 7A. The model depicts the equivalent components of the detector, generally referenced 120, including load impedances 124, thermal sense transistors 130, metal dipole arms 122, and holding arm impedances 126 connected to VDD and 128 connected to ground.

Figure 7B:
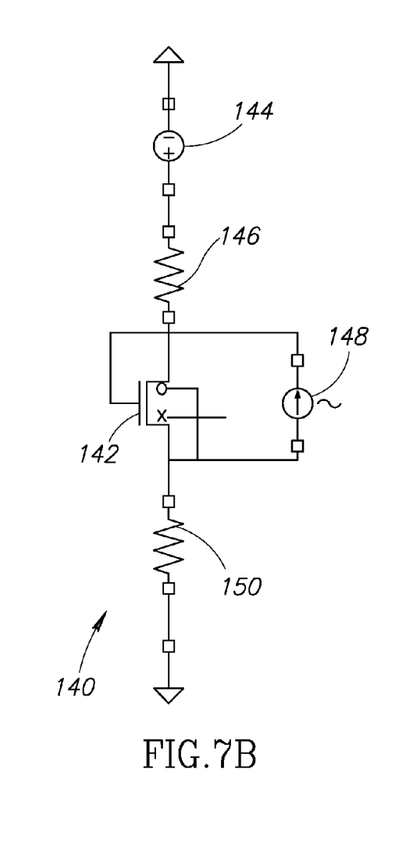
FIG. 7B is the equivalent schematic diagram of the detector of FIG. 4.

The equivalent schematic diagram of the detector of FIG. 4 is shown in FIG. 7B. The equivalent schematic, generally referenced 140, comprises VDD source 144 connected to impedance 146, thermal sense transistor 142 connected to voltage source 148 representing the voltage induced by the antenna dipole elements on the load impedance, and impedance 150. Impedances 146 and 150 are equivalents of the holding arm wire impedances.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. As numerous modifications and changes will readily occur to those skilled in the art, it is intended that the invention not be limited to the limited number of embodiments described herein. Accordingly, it will be appreciated that all suitable variations, modifications and equivalents may be resorted to, falling within the spirit and scope of the present invention. The embodiments were chosen and described in order to best explain the principles of the invention and the practical application, and to enable others of ordinary skill in the art to understand the invention for various embodiments with various modifications as are suited to the particular use contemplated.

What is claimed is:

1. A detector for detecting terahertz (THz) radiation, the detector comprising:
   an antenna having one or more elements supported by a holding arm;
   a load impedance directly coupled to said antenna and operative to convert said terahertz radiation to thermal energy; and
   a thermal sensor operative to generate an electrical signal in accordance with the thermal energy converted by said load impedance, wherein said thermal sensor is located underneath said antenna, and wherein an area of said thermal sensor substantially overlaps the entirety of said antenna.

2. The detector according to claim 1, wherein said thermal sensor comprises a transistor.

3. The detector according to claim 1, wherein said thermal sensor comprises a diode.

4. The detector according to claim 1, wherein said thermal sensor comprises a resistor.

5. The detector according to claim 1, wherein said thermal sensor comprises a device whose current-voltage characteristic is temperature-dependent.

6. The detector according to claim 1, wherein said thermal sensor is substantially covered by said holding arm.

7. The detector according to claim 1, wherein said thermal sensor is under a straight portion of said holding arm.

8. The detector according to claim 1, wherein a size of said thermal sensor is the longest able to fit under said holding arm.

9. The detector according to claim 1, wherein said thermal sensor comprises a transistor whose width substantially fits under said holding arm.

10. The detector according to claim 1, wherein said thermal sensor comprises a transistor whose length substantially fits under said holding arm.

11. The detector according to claim 1, further comprising one or more additional thermal sensors, each placed under a different antenna arm.

12. The detector according to claim 11, wherein said plurality of thermal sensors are connected in parallel so as to increase effective device size.

\* \* \* \* \*